United States Patent [19]
Whitmyer

[11] Patent Number: 5,306,232
[45] Date of Patent: Apr. 26, 1994

[54] HEAD ALIGNMENT SYSTEM
[75] Inventor: Jody J. Whitmyer, Tallahassee, Fla.
[73] Assignee: Whitmyer Biomechanix, Inc., Tallahasse, Fla.
[21] Appl. No.: 12,059
[22] Filed: Feb. 1, 1993
[51] Int. Cl.$^5$ ............................................. A61F 5/00
[52] U.S. Cl. ...................... 602/32; 602/17; 602/36; 482/10
[58] Field of Search .................. 482/10, 95, 131; 602/17, 18, 32–36; 606/241

[56] References Cited

U.S. PATENT DOCUMENTS

| | | |
|---|---|---|
| 1,425,433 | 8/1922 | Zook . |
| 1,556,496 | 10/1925 | Davis . |
| 2,665,685 | 1/1954 | Kaufman . |
| 2,701,564 | 2/1955 | Wilhelm . |
| 2,706,982 | 4/1955 | Hale et al. . |
| 2,712,820 | 7/1955 | Robinson . |
| 2,843,114 | 7/1958 | Hall . |
| 3,118,443 | 1/1964 | Dykinga . |
| 3,359,976 | 12/1967 | Laval, Jr. . |
| 3,741,202 | 6/1973 | Morgan . |
| 4,015,597 | 4/1977 | Beaver . |
| 4,732,144 | 3/1988 | Cunanan . |
| 4,869,240 | 9/1989 | Boren . |
| 5,003,968 | 4/1991 | Mars . |
| 5,010,898 | 4/1991 | de Kanawati et al. . |
| 5,171,295 | 12/1992 | Schwalm, Jr. . |

FOREIGN PATENT DOCUMENTS 311300 3/1919 German Democratic Rep. .

Primary Examiner—Richard J. Apley
Assistant Examiner—Linda C. M. Dvorak
Attorney, Agent, or Firm—Pettis & McDonald

[57] ABSTRACT

A head alignment system for a person having reduced musculature or loss of muscle control of their neck and shoulders, whereby the device maintains the head of the person in a generally upright position. The device comprises at least one pulley attached to a support, a headband having two ends, and a cord having two ends, each of the ends of the cord being adjustably attached to a corresponding one of the ends of the headband. The cord being received by the pulley and the headband and the cord forming an adjustable loop. The loop being adapted for placement about the head of the person, whereby the cord is adjusted so that the head of the person is held generally upright. The cord, by moving about the pulley, permits the headband to move with the head of the person as the person rotates their head about an axis extending from their neck through the top of their head.

8 Claims, 2 Drawing Sheets

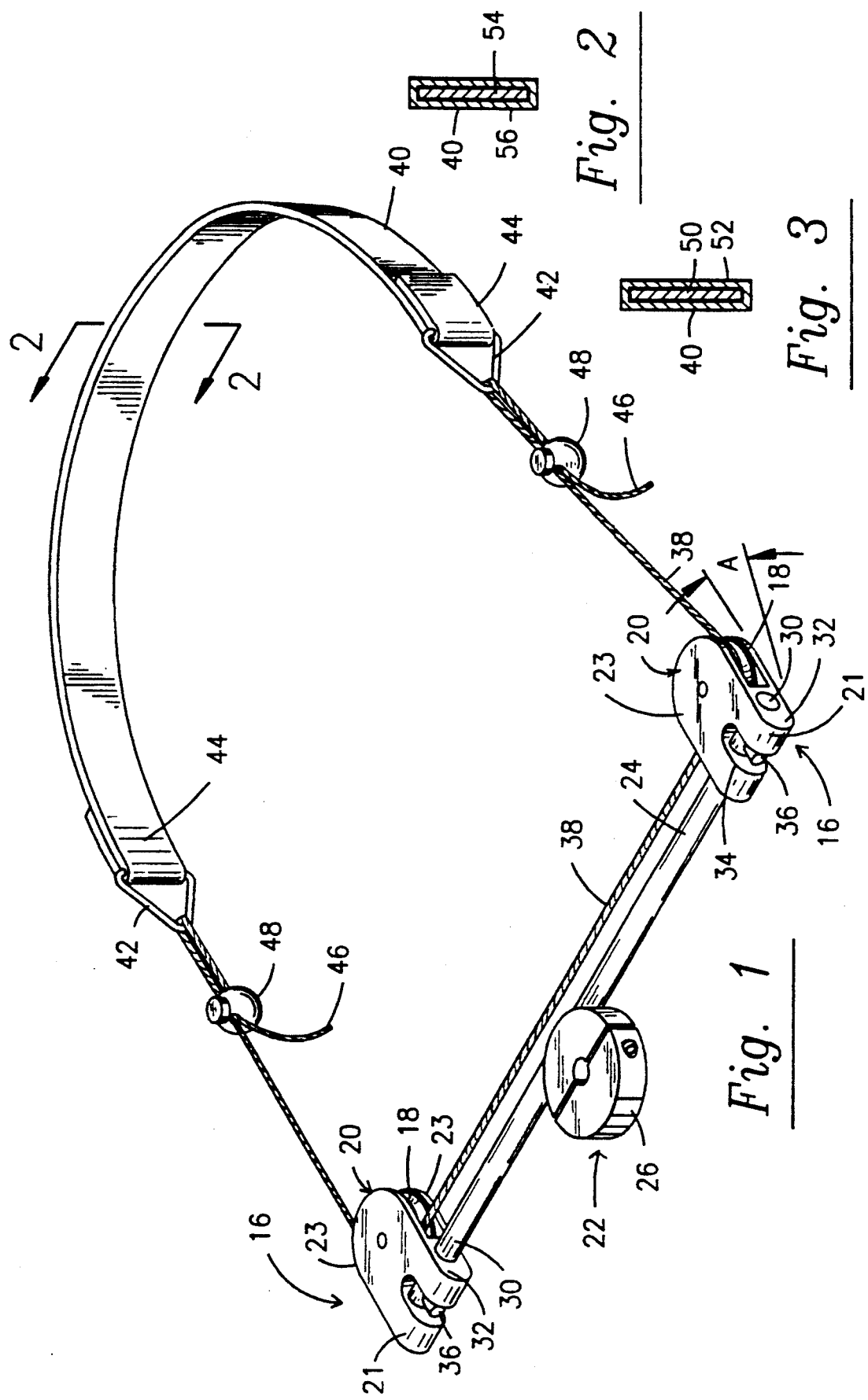

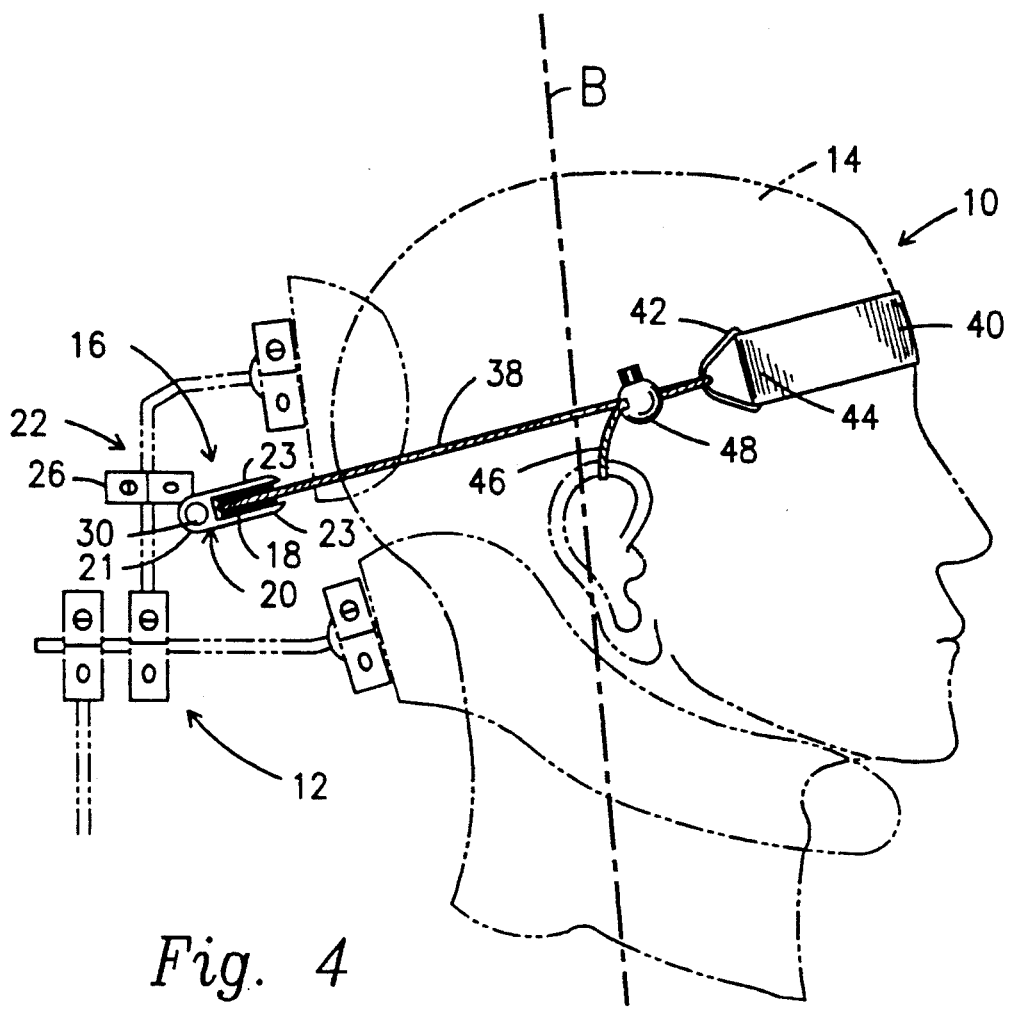
Fig. 4
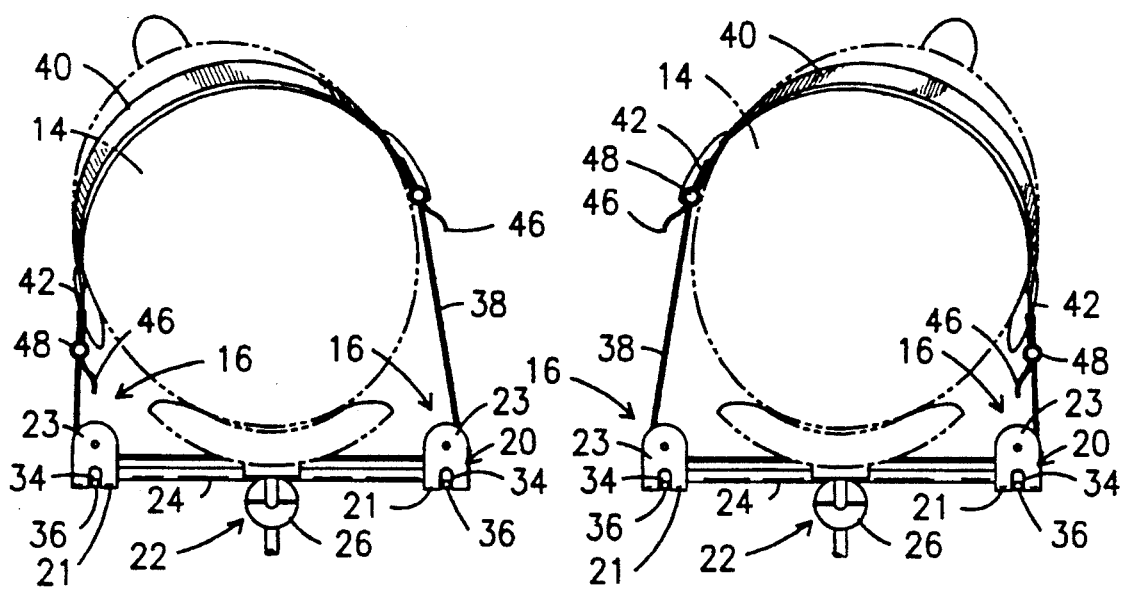
Fig. 5
Fig. 6

HEAD ALIGNMENT SYSTEM

BACKGROUND OF THE INVENTION

1. Field of the Invention

The invention relates to support systems for the physically disadvantaged. More particularly, the invention relates to a device for persons with reduced musculature or muscle control of their neck and shoulders causing their head to droop. The device maintains their head in an upright position.

2. Description of the Prior Art

Many physically challenged individuals have lost muscle tone in the shoulder and neck area or have lost nerve control of the muscles in the shoulder and neck area such that the person's head droops to the front or side. This positioning of the head creates discomfort, restricting their breathing, their ability to talk and communicate with others, and their ability to observe their surroundings. This inability to control the movement of their head can increase the emotional impact of their disability.

A patent issued to Suzanne P. Mars, U.S. Pat. No. 5,003,968, discloses one means for providing head support to such persons. The patent discloses a complex system utilizing a helmet, a collar, chin support straps and elastic tethers. Rotational movement of the head is gained by rotating against an elastic tether.

Head straps and other braces have been used to maintain a patient's head in an upright position; however, the braces are usually very restrictive, permitting little movement. Additionally, support systems that hold the chin in an upward position prevent or restrict the person from eating or speaking.

Notwithstanding the existence of such prior art, it remains clear that there is a need for a head alignment system that has few restrictions and allows some voluntary movement.

SUMMARY OF THE INVENTION

The present invention relates to a head alignment system for supporting the head of a physically challenged person. The system holds the head in a generally vertical position without restricting the movement of the chin or restricting all voluntary movement of the person's head. Most simply stated, the head support system of this invention comprises at least one pulley connected to a support, a headband cord, having two ends, that is operatively received by the pulley, and a headband having two ends, each end being adjustably attached to a corresponding one of the ends of the headband cord. The support may be a wheel chair, a head rest, as shown in the applicant's pending application Ser. No. 07/894,441, or other structure supporting the person. The support helps to maintain the relationship of the head alignment system with the person's head. The headband and the headband cord form an adjustable loop that is placed about the head of the user with the headband being placed on the forehead and the loop being adjusted to the correct size so that an axis extending from the user's neck through the top of the user's head is aligned generally vertically. The headband remains positioned on the user's forehead as the headband cord moves through the pulley when the user swivels his/her head about axis B. The headband maintains the user's head in a firm vertical position, while permitting free rotation of the user's head about the generally vertical axis with little discomfort.

BRIEF DESCRIPTION OF THE DRAWINGS

For a fuller understanding of the nature and objects of the invention, reference should be had to the following detailed description taken in connection with the accompanying drawings, in which:

FIG. 1 is a perspective view of a preferred embodiment of the head alignment system of this invention;

FIG. 2 is a cross sectional view taken along line 2—2 of FIG. 1;

FIG. 3 is a cross sectional view of a second embodiment of the invention as shown in FIG. 2;

FIG. 4 is a left side elevation of the head alignment system, illustrating the system attached to a head support system (shown in phantom) and a person (shown in phantom);

FIG. 5 is a top plan view of the head alignment system illustrating the rotation of the head in a counterclockwise direction, with the head being shown in phantom; and FIG. 6 is a top plan view of the head alignment system illustrating the rotation of the user's head in a clockwise direction, with the head being shown in phantom.

Similar reference characters refer to similar parts throughout the several views of the drawing.

DETAILED DESCRIPTION

A preferred embodiment for the head alignment system of this invention is illustrated in the drawing FIGS. 1, 2, 4–6 and a second embodiment of the headband is illustrated in FIG. 3. The head alignment system is generally indicated as 10 in the views of FIGS. 1, 3–6 and the applicant's head support system disclosed in application Ser. No. 07/894,441 is illustrated in phantom in FIG. 4 and is generally indicated as 12. The head of a user shown as 14 is illustrated in FIGS. 4–6 and is shown in phantom.

Referring first to the view of FIG. 1, it can be seen that the head alignment system 10, in a preferred embodiment, comprises a pair of pulleys, shown generally as 16, each of which further comprises a U-shaped block 20 having a base 21 and a pair of generally parallel legs 23 extending therefrom. A sheave 18 is mounted between the legs 23. The pulleys are 1 to a mounting means shown generally as 22, that, in a preferred embodiment, further comprises a bar 24 and an attaching means 26. In this embodiment, the mounting means 22 is particularly adapted for attachment to the head support system 12. However, in other embodiments, the pulleys 16 may be mounted by other mounting means (comprising clamps, brackets or other means for attachment well known in the art) directly to a support means, such as a wheelchair, a bed, or other well known structures designed to support the user. In a preferred embodiment, two pulleys 16 are used; however, a single pulley, or more than two pulleys, may be used satisfactorily.

In a preferred embodiment, as shown in FIGS. 1, 5 and 6, the pulleys 16 are pivotally mounted to the bar 24, as each block 20 has a bore 30 therethrough sized to receive the bar 24. The amount of rotation of the pulleys 16 about the bar 24 is controlled by a restricting means, conveniently a slot 34 and a pin 36. At the end 32 of the block 20 distal from the sheave 18 is the slot 34 that communicates with the bore 30. The pulleys 16 are mounted to the bar 24 so that they are spaced apart from one another to provide clearance about the user's head 14 as shown in FIGS. 5 and 6. The pin 36 is attached to the bar 24, extending outwardly through the slot 34 as seen in FIGS. 5 and 6. The pin 36, in a preferred embodiment, is threadably attached to the bar 24; however, it may be attached by any suitable means known in the art. The pin 36 permits the block 20 to rotate through a predetermined angle A about the bar 24 as seen in FIG. 1. Angle A, in a preferred embodiment, is approximately 180° even though angle A in FIG. 1 appears much smaller. The rotation of the pulleys 16 permit up and down movement of the user's head 14 without causing pinching of the headband cord 38 within the pulley 16.

The head alignment system further comprises the headband cord 38 which extends through each of the pulleys 16 between the sheave 18 and the block 20. A headband 40 has, in a preferred embodiment, a triangularly shaped member 42 attached to each end 44 of the headband 40. The triangular member 42 is open permitting attachment of the headband 40 to one side of the member 42. Each end 46 of the headband cord is attached to a respective triangular member 42. Each end 46 of the headband cord 46 is looped through a respective member 42 and attached to itself by an adjusting means, conveniently a spring fastener 48. A closed loop is formed by the headband cord 38 and the headband 40 with a predetermined maximum and minimum circumference, the minimum circumference largely determined by the length of the head band 40. In a preferred embodiment, two spring fasteners 48 are used; however, in other embodiments, one end 46 of headband cord 38 could be directly attached to the headband 40 leaving a single spring fastener 48 to make the necessary adjustments.

The bar 24, mounting means 26, and the pulleys 16 are constructed of steel in a preferred embodiment; however, they may be constructed of plastic or any other suitable material having the strength characteristics required. The cord 38 may be comprised of woven nylon or other suitable materials. The headband 40 in the preferred embodiment is comprised of a stretchable material 50 similar to Rubatex ®, with a covering of a terry cloth material 52 as shown in FIG. 2. This construction is used for an individual who has little strength in their neck and shoulder muscles and is considered "floppy." A second embodiment uses a stretch webbing material 54, similar to Darlexx ® that is covered with a stretch fabric 56, similar to Lycra ®. The second embodiment is used with those individuals who pull forward with a strong pull against the strap, such as persons who have tone problems associated with traumatic brain injuries and dominant flexer patterns.

Having thus set forth a preferred construction for the head alignment system 10 of this invention, it is to be remembered that this is but a preferred embodiment. Attention is now invited to a description of the use of the head alignment system 10. Care must be taken to ensure the proper relationship between the alignment system and the user as situated in his/her support means. The alignment system 10 must be mounted either on a head support system similar to that shown in FIG. 4 or directly to a wheelchair or other structure providing support to that individual at the proper height and proper tightness to ensure the safety and comfort of the user. The pulleys 16 must be spaced far enough apart so that the headband cord 38 remains clear of the user's head, particularly the ears and other sensitive areas. The headband cord 38 is passed around each sheave 18 between the sheave 18 and the block 20 permitting free movement of the headband cord 38. Each end of the headband cord 38 is attached to a respective member 42 using the spring fasteners 50. The user's head is placed in an upright position so that Axis B extending from the neck and through the top of the head is generally vertical. The headband 40 is then placed about the forehead of the user's head 14 and the head band cord 38 is tightened sufficiently to prevent the headband from slipping over the user's eyes or down beneath the user's chin. The height of the pulleys 16 in relation to the user's head 14 will also dictate whether the headband 40 will have the tendency to slip over the user's eyes or slip off the user's head 14.

Now that the head alignment system 10 has been mounted and properly adjusted to the user's head 14, the user will find that he may freely rotate his head about the generally vertical Axis B as the cord moves about the sheaves 18 of the pulleys 16. The stretchability of the headband 40 permits some movement in the forward and backward direction, and yet firmly holds the user's head 14 in the upright position.

It will thus be seen that the objects set forth above among those made apparent from the preceding description, are efficiently attained and, since certain changes may be made in the above article without departing from the scope of the invention, it is intended that all matter contained in the above description, or shown in the accompanying drawings, shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. A head alignment system suitable for attachment to a support system comprising:
   at least one pulley having mounting means adapted to be connected to a support;
   a headband cord having two ends, a portion of said cord being intermediate said two ends, said intermediate portion of said cord being received by said pulley; and
   a headband having two ends, each one of said ends being attached to a corresponding one of said ends of said cord such that said headband and said cord form a loop, whereby said loop is adapted for placement about the head of a person, whereby said alignment system holds the head of the person upright while permitting rotational movement of the head about an axis extending from the neck upwardly through the top of the head of the person.

2. A head alignment system as in claim 1 further comprising a mounting means, comprising:
   a bar upon which is mounted said pulley, said bar having an attaching means attached thereto for attachment to the support.

3. A head alignment system as in claim 2 wherein said pulley is pivotally mounted to said bar, said head alignment system further comprising a pulley rotation restricting means, whereby said pulley may only rotate about said bar through a predetermined angle of rotation.

4. A head alignment system as in claim 3 wherein said pulley comprises;

a generally U-shaped block having a base and a pair of legs extending therefrom, a sheave being mounted between said legs, said base having a bore extending therethrough generally parallel with said sheave, said bore sized to receive said bar such that said pulley is rotatable about said bar; and wherein said restricting means comprises a slot extending through said base at right angles to and in communication with said bore, and a pin attached to said bar extending outwardly therefrom through said slot, whereby said slot restricts movement of said pin and thus rotation of said pulley about said bar.

5. A head alignment system as in claim 1 comprising a second pulley having mounting means adapted to be connected to the support, said headband cord being operatively received by said second pulley.

6. A head alignment system as in claim 1 wherein said headband cord further comprises at least one adjustment means, whereby said loop may be adjusted between a predetermined maximum and a predetermined minimum circumference.

7. A head alignment system as in claim 1 wherein said headband comprises a stretchable webbing material covered by a second stretchable material.

8. A head alignment system as in claim 1 wherein said headband comprises a stretch material covered by an absorbent material.

* * * * *